United States Patent
Paulitschke et al.

(10) Patent No.: US 6,946,290 B2
(45) Date of Patent: Sep. 20, 2005

(54) METHOD FOR THE DETERMINATION OF THE CONFLUENCE OF A CELL LAYER ON POROUS BIOMATERIALS

(75) Inventors: Manrico Paulitschke, Berlin (DE); Axel Koepenik, Berlin (DE)

(73) Assignee: VasoTissue Technologies GmbH, Berlin (DE)

(*) Notice: Subject to any disclaimer, the term of this patent is extended or adjusted under 35 U.S.C. 154(b) by 224 days.

(21) Appl. No.: 10/307,773

(22) Filed: Dec. 2, 2002

(65) Prior Publication Data

US 2003/0077574 A1 Apr. 24, 2003

Related U.S. Application Data

(63) Continuation of application No. PCT/DE01/02109, filed on Jun. 1, 2001.

(30) Foreign Application Priority Data

Jun. 2, 2000 (DE) .......................................... 100 28 118

(51) Int. Cl.[7] .................................................. C12N 5/00
(52) U.S. Cl. ........................ 435/325; 435/395; 435/401; 435/4
(58) Field of Search ................................ 435/325, 395, 435/401, 4

(56) References Cited

U.S. PATENT DOCUMENTS 4,911,713 A    3/1990    Sauvage et al.

FOREIGN PATENT DOCUMENTS

| FR | 2 665 175 | 1/1992 |
| WO | WO 93 01843 | 2/1993 |
| WO | WO 97 49799 | 12/1997 |

OTHER PUBLICATIONS

1994, Rapid Visualization of Viable and Nonviable Endothelium on Cardiovascular Prosthetic Surfaces by Means of Fluorescent Dyes C. Gillis, A Haegerstrand et al., J. Thorac. Cardiovascular Surgeon, 108, 1043–1048.
1991, 111–Indium is an Unreliable In Vivo Label for Vascular Endothelial Cells, M.B. Herring et al., Ann Vasc. Surg. 5, 424–428.
1984, Manual of Histological Techniques, Churchill Livingstone, Edinburgh J. D. Bancroft et al.
1994, A New, Automated and Accurate in Vitro Method to Quantify Endothelial Cells Attached to Vascular Prostheses, M.J.T. Visser et al., Thrombosis and Haemostasis, 72 (1), 146–150.

*Primary Examiner*—Leon B. Lankford, Jr.
(74) *Attorney, Agent, or Firm*—Jordan and Hamburg LLP

(57) ABSTRACT

The invention relates to a novel method, permitting the semiquantitative determination of the confluence of a cell layer on the total surface of a porous biomaterial, without irreversible damage to part or indeed all of the hybrid construct. A method is described for the first time, which is able to detect the formation of the confluence or the confluence itself, without destroying the hybrid construct, and thus permits the finished hybrid product to be withdrawn from the essential growth conditions only after the determination of the completed confluence, and to immediately direct it to its further use.

10 Claims, 1 Drawing Sheet

Figure 1:
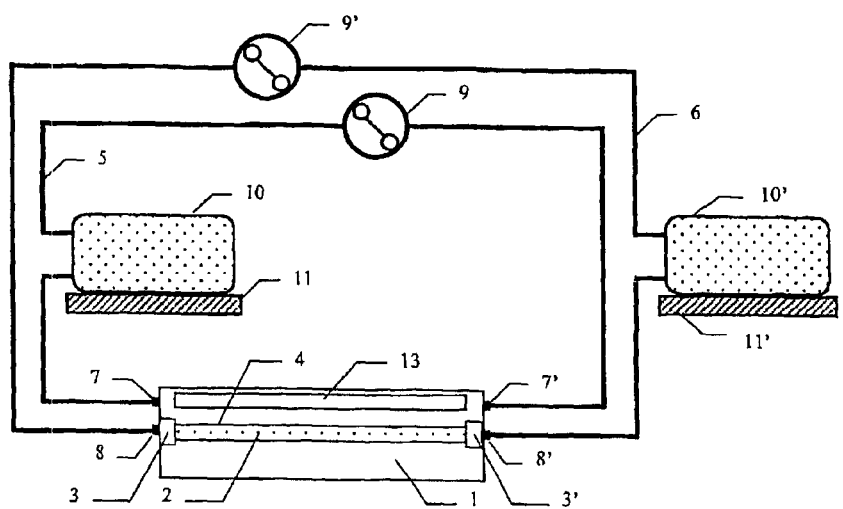

METHOD FOR THE DETERMINATION OF THE CONFLUENCE OF A CELL LAYER ON POROUS BIOMATERIALS

DESCRIPTION

The invention relates to a novel method for the semiquantitative determination of the confluence state of a cell layer on the entire surface of a porous biomaterial, which can be made of synthetic matters, as well as of natural materials, and exhibits a biological tolerance with respect to the cell layer. By coating or soaking the porous material with the cell culture, a hybrid construct hereby arises, the functionality of which depending decisively from the continuity degree of the cell layer, i.e. the confluence state of the cell layer applied.

Methods for the direct determination of the confluence state of a cell layer on biomaterials are known. In this case, methods are concerned in which the cells are radioactively marked, visually inspected by means of cell dyeing and light micrography or are examined using immunohistological methods (C. Gillis, A. Haegerstrand et al., Rapid visualization of viable and nonviable endothelium on cardiovascular prosthetic surfaces by means of fluorescent dyes, J. Thorac. Cardiovasc. Surg. 1994, 108: 1043–1048; M. B. Herring et al., 111-Indium is an unreliable in vivo label for vascular endothelial cells, Ann. Vasc. Surg. 1991, 5: 424–428). In the document U.S. Pat. No. 4,911,713, a method for the complete chemical sealing of a porous vessel prosthesis is described. The determination of the tightness in this case ensues through the perfusion of two independent circuits, with a through-flow of the wall being artificially generated by means of a pressure difference.

The documents WO 97/49799 A1 and WO 93/01843 A1 describe methods in which cells are cultivated on porous materials. The porosity of the vessel prosthesis, as it is shown in these publications, obviously is all the more greater, the fewer inter-cell contacts exist between the cells.

Often, the construction of the biomaterial causes conditions that do not allow an unimpeded assessment of the cell layer all over the entire surface without the cell layer being exposed in advance by means of mechanical changes on the hybrid construct. The known dyeing techniques for detecting the cell structures on the hybrid construct have a cytotoxic action and therewith lead to an irreversible cell damage (J. D. Bancroft et al., Manual of histological techniques, Edinburgh: Churchill Livingstone 1984; M. J. T. Visser et al., A new automated and accurate in vitro method to quantify endothelial cells attached to vascular prostheses, Thrombosis and Haemostasis, 1994, 72 (1): 146–150).

All of these methods share the important disadvantage that the exposure and dyeing of the cell layer, to be able to visually inspect them in an unimpeded manner, entails a functional destruction of the hybrid construct. This results in an irreversible damage of the hybrid construct, for one, by mechanical interventions in order to expose the surface to be examined, and, for another, cytotoxic damages arise on the hybrid construct by the agents used precluding a further use of the examined segment for the actual target application.

So as to be able to make a secure statement on the confluence state of the cell layer over the entire surface of the hybrid construct, either the entire surface or, as in the known methods, a representative partial segment has to be examined. The first case includes the already depicted irreversible damage of the hybrid construct; the latter includes the high risk of transferring the results of a partial segment to the entire hybrid construct surface to be observed. For this reason, a demand for a reliable method for determining the cell density over the entire hybrid construct surface, without having to influence or even destroy the created construct in its functionality, has existed for a long time.

The object of the invention is to propose a method that allows statements to be made on the confluence state of a cell layer on or in a porous biomaterial, and which overcomes the mentioned disadvantages of the known techniques.

The object has been solved in that the biomaterial is fixed as a permeable boundary layer in a two-chamber system—FIGS. (FIG.) 1 and 2—(1, 2) by means of culture medium-impermeable adapters (3, 3'), whereby the complete wetting of the cell-coated biomaterial with culture medium has to be guaranteed over the entire measurement period. The initially existing porosity of the biomaterial (4) acting as a separation layer between the two chambers thereby enables the direct diffusion of the culture medium between chamber A (1), which is operated as a static chamber filled with culture medium and has a pressure compensation means (11) or connections (7, 7') to a perfusion circuit (5), and a chamber B (2) connected to a perfusion circuit (6) via the connections (8, 8'). The perfusion circuits (5, 6) each are comprised of a pumping means (9, 9') for independently controlling the two perfusion circuits (5, 6), and a culture medium reservoir (10, 10'), which also acts as a pressure compensation vessel, which are interconnected by tubes.

The higher dynamic pressure generated by the higher perfusion in chamber B (2') leads to the reduction of the overall pressure in chamber B and therewith to a transverse flow through the wall of the porous biomaterial (4) from chamber A (1) in the direction of chamber B (2), which transverse flow varies depending on the porosity degree of the biomaterial. In this case, attention has to be paid that the two circuits are controlled in such a manner that the dynamic pressure in circuit 5 always remains lower than in circuit 6, which can most easily be achieved by operating chamber A (1) as a static unit. The physical basis for this is Bernoulli's law, according to which the static pressure in flowing liquids is lower than that in static liquids. When a connection between both of them exists, an inflow of liquid from the static liquid field into the throughflowed liquid field takes place. The culture medium passed over into the perfused chamber B (2), is carried away by the flow of culture medium and collects in the external culture medium reservoir (10') of the perfusion cycle (6). Thereby the volume portion in the perfused segment of the chamber does not increase. A balance over the entire measurement chamber therefore entails a volume loss of culture medium, and, at the same time, the intake of gas molecules of an identical volume into chamber A (1). The formation of a closed cell layer on the porous biomaterial (4) corresponds to the formation of a simple diffusion barrier with respect to the flow between the two chamber segments. The cell layer has the function of a barrier on the biomaterial, which prevents the perfusion-contingent transverse flow. With the cell density increasing, the volume flow through the wall of the biomaterial decreases, which is reflected by a distinct reduction of the volume loss in the non-perfused segment. Upon reaching the confluence of the cell layer on the biomaterial surface, the volume loss asymptotically approaches a stationary balance on a low and constant level. The culture medium transverse flow from chamber A (1) into chamber B (2), conditioned by the different density of the culture medium volume exiting from chamber A (1) and a gas volume entering in an identical volume, characterized by a constant decrease of the weight of the two-chamber system comprised of chamber A (1) and chamber B (2), hence can be most precisely detected measurement-technically via a determination of the weight of the entire chamber using a balance (11). From the measured weight reduction, the volume portion passed over can be calculated and figured in time-dependence in a volume flow development curve. Since said curve reflects at the same time the existing number of the still permeable pores of the biomaterial that hence are not yet covered with a cell layer, semiquantitative statements on the confluence state can be made from the measured values. Identical statements on the volume loss in chamber (A) can be made via a level indicator (13). Alternatively, the volume increase in the culture medium reservoir (10') of perfusion circuit (6) or the volume decrease in the culture medium reservoir (10) of perfusion circuit (5) may also be determined by the same methods.

The determination of the confluence may likewise ensue in that chamber A (1), as well as chamber B (2), are perfused for forming the confluence. For the determination of the confluence, however, circuit (5) connected to chamber A (1) has to be perfused with a lower dynamic pressure, which in the static case recedes down to zero.

The essence of the invention resides in a method for the semiquantitative determination of the confluence of a cell layer on porous biomaterials, in which with an increasing confluence of a cell layer on the biomaterial that is fixed between two perfusable chambers as a boundary layer, the transverse flow through the biomaterial wall is reduced, with the volume flow measurement technically being detected as an indicator for the confluence state. Thereby, the transverse flow is generated by flow speeds that are different in the two chambers A and B and may be configured time-constant or varying.

In an advantageous manner, the biomaterial is pretreated with substances enhancing the cell adhesion, for an improved adhesion of the cells while maintaining the porosity. The colonization of the biomaterial takes place by coating or soaking with one or various cell culture/s.

The confluence of the cell layer is already achieved during the coating or by the growth of the cells under static or under flow conditions. According to the invention, the determination of the confluence takes place by determining the weight of a culture medium reservoir or via a level indicator.

The perfusion circuits (5, 6) may be operated in cocurrent or countercurrent flow.

By means of the permanent semiquantitative acquisition of measured values, a reliable statement on the confluence state of the cell layer on the entire surface of the biomaterial may surprisingly be made without being compelled to destroy the hybrid construct, and without neglecting areas of the hybrid construct formed, which cannot be examined by destruction-free methods for determining the confluence state.

The features of the invention become apparent from the elements of the claims and from the description, with single features, as well as several features in the form of combinations representing advantageous embodiments, for which protection is applied for with the present document.

In the mentioned publication U.S. Pat. No. 4,911,713, a method for the complete chemical sealing of a porous vessel prosthesis is described: The determination of the tightness ensues via the perfusion of two independent circuits, with a through-flow of the wall being artificially generated by a pressure difference. In this case, one starts from the approach that when no pressure difference arises or cannot be maintained between the two perfusion circuits, the prosthesis is untight and not usable (column 6, lines 3 through 9). The determination of the porosity takes place by means of a measurement of a pressure difference between the inner and outer lumen, with the arising pressure difference exclusively permitting a statement on the complete or incomplete seal, the pressure difference or the existence thereof hence representing a function, and therewith the decisive parameter with respect to porosity.

However, the approach according to the invention is of a physically completely different origin: Independent of the fact whether the prosthesis is porous or almost or even completely sealed, a pressure difference exists between the inner and outer circuit, which, nevertheless, is not at all a function of porosity. The pressure difference in the solution described according to the invention is solely given in that, for one, the pressure in the unperfused state is exclusively determined by the height of the fluid column and the density, which pressure thus showing identical values at any segment observed of the prosthesis in a comparison between inside and outside. On the other hand, dynamic pressures arise in addition to these static pressures in the two circuits by different perfusion rates, the values of which dynamic pressures being proportional to the flow rate and hence resulting, with different perfusion conditions, in different dynamic pressures. The stability of the total pressure as a sum of static and dynamic pressure then leads, according to Bernoulli, to a difference with respect to the static pressures and, as a result, to a transverse flow through the prosthesis wall.

For this reason, even a pressure measurement such as described in the document U.S. Pat. No. 4,911,713, might not furnish any statement whatsoever with respect to the unsealed state or the porosity of the prosthesis wall, since by means of the inventive solution, a complete seal and a complete prevention of a transverse through-flow of the prosthesis wall by the cells are not imaginable. The application corresponding to said U.S.-publication thus (column 6, lines 3–9) would lead to an immediate pressure compensation, independent of the degree of confluence of the cell layer. The prosthesis therewith could quasi never be designated as being completely sealed or confluently colonized or partially colonized.

The mentioned documents WO 97/49799 A1 and WO 93/01843 A1 describe methods in which cells are cultured on porous materials: The porosity of the vessel prosthesis, as depicted in these publications, obviously is all the more greater, the fewer inter-cell contacts exist between the cells. If one intended to conclude from this that a prosthesis with a cell layer of higher density obviously causes another pressure difference than a prosthesis with a cell layer of less density and hence of higher porosity, then this is certainly the case with respect to the document U.S. Pat. No. 4,911,713, but not as far as the present inventive solution is concerned.

The methods according to U.S. Pat. No. 4,911,713, WO 97/49799 A1, and WO 93/01843 A1 pursue a physically completely different background as compared to the present inventive solution, and the combination of the patent publications mentioned does not obviously lead to the methods according to the invention.

The advantageous differences of the inventive solution relative to the prior art reside in that it is for the first time possible using the method according to the application to directly measure the decrease of porosity and hence the increase of inter-cell contacts over the entire prosthesis, without withdrawing the cell-colonized prosthesis from the circuit system, dyeing it in parts or examining it otherwise, and to then make vague conclusions from a partial segment to the entire state of the prosthesis.

The invention will now be described in more detail by means of exemplary embodiments, without being restricted to these examples.

EXEMPLARY EMBODIMENTS

Example 1

Figure 2:
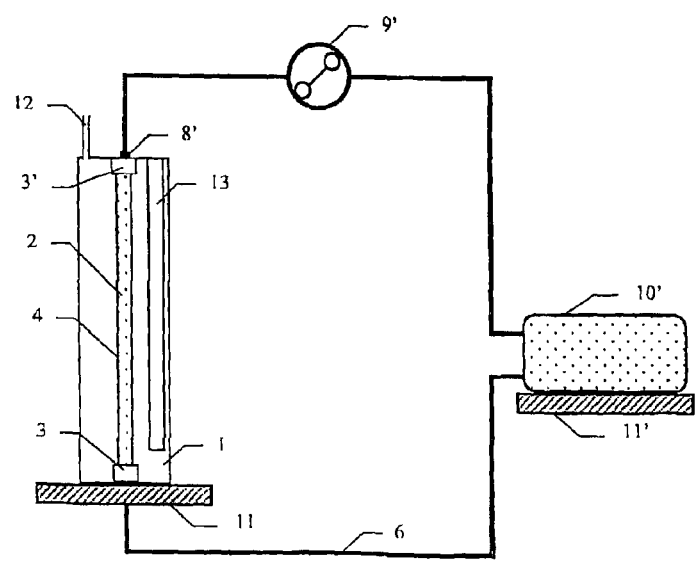

In a two-chamber system, a porous biomaterial (FIG. 2: 4) is fixed between the two chambers (FIG. 2: 1, 2), which features an initial subconfluent cell density on the biomaterial by soaking with a cell culture. Subsequently, chamber B (FIG. 2: 2) is operated under constant perfusion via the perfusion circuit (FIG. 2: 6) so as to reach the confluence state of the cells on the surface of the hybrid construct. Chamber A (FIG. 2: 1) is statically operated and disposes of a pressure compensation means (FIG. 2: 12). By way of a weight determination (FIG. 2: 11) of the two-chamber system, the formation of the closed cell layer is semiquantitatively detected via the volume passage through the biomaterial (FIG. 2: 4).

Example 2

In a two-chamber system, a porous biomaterial (FIG. 2: 4) is fixed between the two chambers (FIG. 2: 1, 2), which features an initial subconfluent cell density on the biomaterial by soaking with a cell culture. Subsequently, chamber B (FIG. 2: 2) is operated under a varying perfusion, so as to reach the confluence state of the cells on the surface of the hybrid construct. Chamber A (FIG. 2: 1) is statically operated. Via a level indicator (FIG. 2: 13) within chamber A (FIG. 2:1) or by means of a weight determination (FIG. 2: 11) of the two-chamber system with inclusion of the perfusion rates, the formation of the closed cell layer is semiquantitatively detected in dependence of the volume passage through the biomaterial.

Example 3

In a perfusion chamber A (FIG. 1: 1), a porous biomaterial (FIG. 1: 4) formed into a vessel prosthesis, is fixed, whereby the chamber B (FIG. 1: 2) is formed inside of the vessel prosthesis. After coating with a cell culture, the biomaterial features an initial subconfluent cell density. Subsequently, the entire chamber system (FIG. 1: 1, 2) is operated via the perfusion circuits (FIG. 1: 5, 6) under a varying perfusion, so as to reach the confluence state of the cells on the surface of the hybrid construct. The check of the confluence state ensures by a measurement of the filling level (FIG. 1: 13) or by a weight determination (FIG. 1: 11) of the culture medium reservoir associated to chamber B (FIG. 1: 10'), after the perfusion in chamber A (FIG. 1: 1) has been stopped and same is further operated statically or with a lower dynamic pressure as compared to chamber B (FIG. 1: 2).

Example 4

In a perfusion chamber A (FIG. 1: 1), a porous biomaterial (FIG. 1: 4) formed into a vessel prosthesis, is fixed, whereby the chamber B (FIG. 1: 2) is formed inside of the vessel prosthesis. After coating with a cell culture, the biomaterial features an initial subconfluent cell density. The check of the confluence state ensues by a measurement of the filling level (FIG. 1: 13) or a weight determination (FIG. 1:11) of the culture medium reservoir (FIG. 1: 10) of chamber A (FIG. 1: 1) via the perfusion circuit (FIG. 1: 5), which is operated statically or with a lower dynamic pressure as compared to chamber B (FIG. 1: 2).

LIST OF REFERENCE NUMERALS 1 chamber A
2 chamber B
3, 3' adapter
4 biomaterial
5 perfusion circuit of chamber A
6 perfusion circuit of chamber B
7, 7' tube connections of chamber A
8, 8' tube connections of chamber B
9, 9' pumping means
10, 10' culture medium reservoir
11, 11' balance
12 pressure compensation
13 level indicator

What is claimed is:

1. A method for determining a confluence of a cell layer on a porous biomaterial, the method comprising:

obtaining a system having first and second perfusable chambers;

fixing said biomaterial between said perfusable chambers, said biomaterial defining a boundary for said cell layer;

providing an initial coating of said biomaterial with said cell layer;

providing a volumetric flow of liquid through at least one of said two perfusable chambers;

measuring a change of transverse flow of said liquid over time through said biomaterial;

based on said change in transverse flow over time, determining a confluence of said cell layer on said biomaterial surface; and wherein an increased confluence of said cell layer on said biomaterial is indicated by a reduced transverse flow through said biomaterial.

2. The method according to claim 1, comprising:

providing a volumetric flow of liquid through both of said two perfusable chambers, said volumetric flows having different volumetric flow rates, wherein one or both of said flows is time-constant or time varying; and wherein said transverse flow generated by said different flow rates.

3. The method according to either of claim 1 or 2, wherein said biomaterial is pretreated for adhesion of said cells.

4. The method according to claim 1 or 2, wherein colonization of said biomaterial occurs by coating or soaking said biomaterial with at least one cell culture.

5. The method according to claim 1 or 2, wherein confluence occurs by coating or by growth of said cells under a static condition or a flow condition.

6. The method according to claim 1 or 2, wherein said system has a culture medium reservoir, said reservoir having a weight, and said determination of confluence occurs by monitoring said weight of said culture medium reservoir.

7. The method according to claim 1 or 2, wherein said system has a level indicator and said confluence being measured with said level indicator.

8. The method according to claim 1 or 2, wherein:

said first chamber comprises pressure compensation means, said first chamber being statically operated;

said second chamber comprises culture medium-impermeable adapters;

said system further comprises;
(1) a perfusion circuit, said perforation circuit being connected to said medium-impermeable adaptors of said second chamber, said perfusion circuit having pumping means for controlling said perfusion circuit;
(2) a culture medium reservoir, said culture medium reservoir being connected to said perfusion circuit, said culture medium reservoir adapted to being a pressure compensation vessel, said culture medium reservoir storing culture medium; and
wherein said method comprising the step of wetting said cell-coated biomaterial with said culture medium from said reservoir during a predetermined measurement period.

9. The method according to claim 1 or 2, wherein:
said first chamber comprises connection points;
said second chamber comprises culture medium-impermeable adapters;
said system further comprises:
(1) first and second perfusion circuits, said first perforation circuit being connected to said connection points of said first chamber and said second perforation circuit being connected to said medium-impermeable adaptors of said second chamber;
said first and second perfusion circuits each having first and second pumping means for independently controlling said first and second perfusion circuits;
(2) first and second culture medium reservoirs, said first and second culture medium reservoir being respectively connected to said first and second perfusion circuits, said first and second culture medium reservoirs adapted to being respective first and second pressure compensation vessels, said first and second culture medium reservoirs storing a culture medium;
wherein said method comprising the step of wetting said cell-coated biomaterial with said culture medium from one of said first and second reservoirs during a predetermined measurement period.

10. The method according to claim 9, wherein said perfusion circuits are operated in concurrent or countercurrent flow directions.

* * * * *